United States Patent [19]
Burton et al.

[11] 4,330,486
[45] May 18, 1982

[54] BIS(PHOSPHONIC ACID) DIFLUOROMETHANE

[75] Inventors: Donald J. Burton, Iowa City, Iowa; Richard M. Flynn, Bethesda, Md.

[73] Assignee: University of Iowa Research Foundation, Iowa City, Iowa

[21] Appl. No.: 143,995

[22] Filed: Apr. 28, 1980

[51] Int. Cl.$^3$ .............................. C07F 9/38; C07F 9/40
[52] U.S. Cl. .............................. 260/502.4 P; 260/932; 260/970
[58] Field of Search ................ 260/932, 502.4 P

[56] References Cited

U.S. PATENT DOCUMENTS 3,422,021 1/1969 Roy ..................................... 260/932
3,662,039 5/1972 Nicholson ........................... 260/932

FOREIGN PATENT DOCUMENTS 1263934 2/1972 United Kingdom

OTHER PUBLICATIONS

Chambers, "Fluorine in Organic Chemistry", J. Wiley & Sons, New York, (1974), p. 41.
Hudlicky, "Chemistry of Organic Fluorine Compounds", (1962) MacMillan Co., New York, pp. 72-73.

Primary Examiner—Anton H. Sutto
Attorney, Agent, or Firm—Beveridge, DeGrandi & Kline

[57] ABSTRACT

Fluorine-containing phosphonates and phosphonic acids are described. The method of preparation is a reaction of trialkylphosphites with dihalodifluoromethanes or a reaction of the salts of dialkylphosphites with halodifluoromethylphosphonates. The corresponding phosphonic acids are prepared by hydrolysis of the phosphonates.

1 Claim, No Drawings

BIS(PHOSPHONIC ACID) DIFLUOROMETHANE

The invention described herein was made in the course of work under a grant or award from the Department of Health, Education and Welfare.

SUMMARY OF THE INVENTION

The present invention relates to fluorine-containing phosphonates and phosphonic acids and methods of preparing same. In particular, the fluorine-containing phosphonates are characterized by the formula:

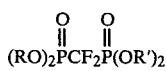
$$(RO)_2PCF_2P(OR')_2$$

wherein R is an alkyl group from 1 to 16 carbon atoms, preferably from 1 to 6 carbon atoms.

These compounds are diphosphonates and have been prepared by one of two methods.

Thus, the compounds of the invention may be prepared by the following sequence:

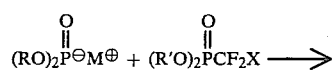
(a)

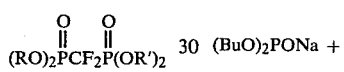

wherein M is an alkali metal, preferably

Na or K

X is a halogen, preferably Cl, Br, or I

As an alternative, the compounds may be prepared thusly

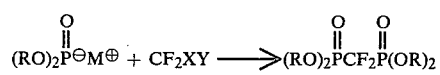
(b)

wherein X is a halogen as before defined, and Y is halogen, preferably Cl Br and I; and M and R as defined above.

The corresponding acid is made by hydrolysis of the phosphonate compound by known means.

Typically, the reaction between $(BuO)_2 P(O)CF_2Br$ and $(BuO)_2PONa$ in hexane was found to yield tetrabutyl difluoromethylene bis(phosphonate) (1) in 47% isolated yield. A 27% yield of the reduced dibutyl monophosphonate was also isolated. The spectral and analytical data of the bis (phosphonate) were entirely compatible with the structural assignment. (Bu is butyl)

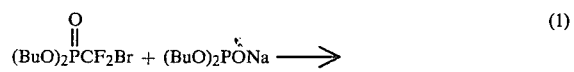
(1)

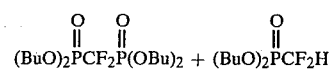

Similarly, the reaction between $(EtO)_2P(O)CF_2Br$ and sodium diethyl phosphite in hexane afforded tetraethyl difluoromethylene bis(phosphonate (2) in 13% isolated yield. (Et is ethyl). The considerable difference in yields between (1) and (2) can probably be ascribed to the solubility differences of their corresponding sodium dialkyl phosphites. Sodium dibutyl phosphite is freely soluble in hexane, whereas sodium diethyl phosphite is much less soluble. No effort has been made to entirely optimize either of these reactions and high isolated yields are undoubtedly possible. The mechanism for these reactions can be viewed as abstraction of positive bromine from the initial phosphonate followed by recombination.

$$(BuO)_2\overset{O}{\overset{\|}{P}}CF_2Br + (BuO)_2PONa \longrightarrow$$

$$(BuO)_2\overset{O}{\overset{\|}{P}}CF_2{}^\ominus Na^\oplus + Br-\overset{O}{\overset{\|}{P}}(OBu)_2 \longrightarrow (1)$$

The mechanism is, however, more complex. The reaction between sodium dibutyl phosphite and $(EtO)_2P(O)CF_2Br$ afforded three bis(phosphonates) as observed in the $^{19}F$ nmr spectrum in a 1:2:1 ratio.

Generally, the reaction is carried out in an inert, hydrocarbon, non-protic solvent. This reduces the amount of reduction product formed in the reaction. Particularly good results were obtained using toluene.

$(BuO)_2PONa +$

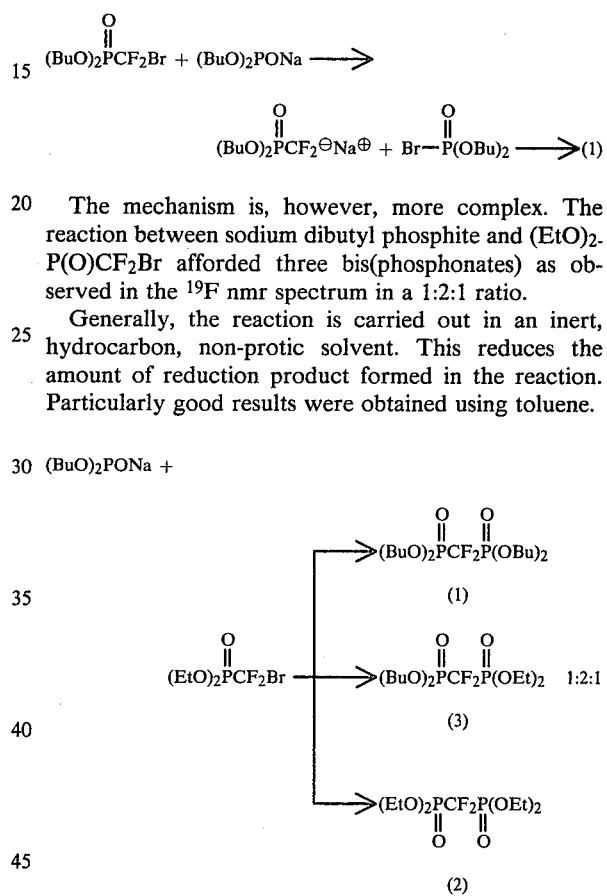

Two of these bis(phosphonates) were identified as (1) and (2) by enhancement of their respective signals in the $^{19}F$ nmr spectrum upon addition of authentic samples of each. The remaining triplet was assigned the mixed bis(phosphonate) structure (3). Fortunately, (2) was both considerably more water soluble and lower boiling than either (1) or (3) and was entirely removed in the workup of the reaction mixture. The unsymmetrical bis(phosphonate) (3) could not be separated entirely from (1). The $^{19}F$ nmr spectrum of the mixture showed two triplets: $\delta = 121.7$ J=87 Hz (3) and $\delta = 121.4$ J=87 Hz (1). The $^{31}P$ nmr spectrum showed only a triplet. The $^1H$ nmr spectrum clearly indicated the presence of an ethyl group. Finally, the $^{13}C$ nmr spectrum revealed all seven carbons for the alkyl groups of (3) as well as a (t,t) for the difluoromethyl ene carbon atom. The butyl carbons of (3) did, however, overlap with the butyl carbons of (1). A rationale for the observations of the three bis-(phosphonates) is shown in the equation below:

Mechanistic scheme for the reaction between (BuO)₂PONa and (EtO)₂P(O)CF₂Br

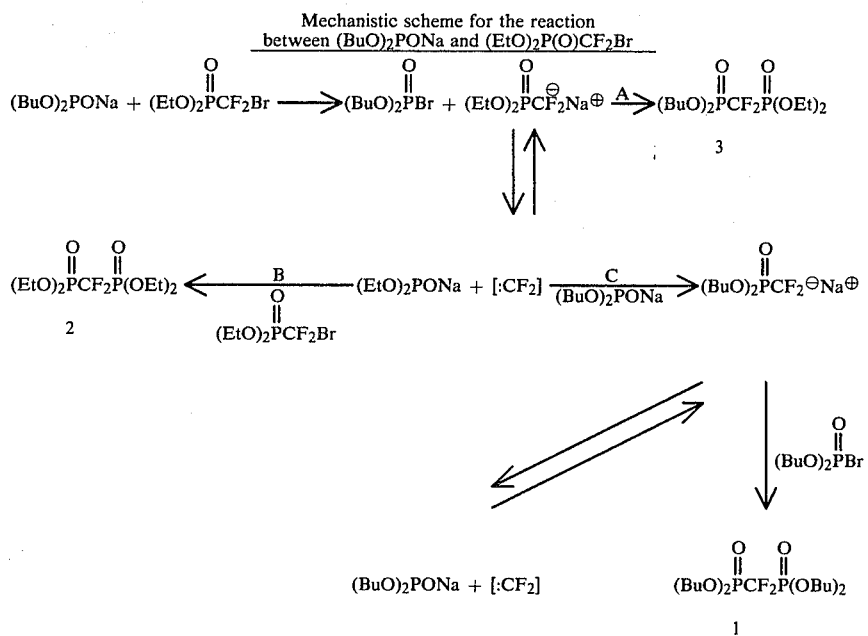

In path [A] the recombination of the phosphonate ylide and the acid bromide lead directly to the mixed phosphonate 3. If, instead of recombination, the ylide were to collapse to [:CF₂] and (EtO)₂PONa, two alternate pathways arise. In path [B], the (EtO)₂PONa can react directly with the precursor phosphonate to afford 2. In path [C], the [:CF₂] can be trapped by the (BuO)₂PONa to afford the dibutyl ylide which can then react further with the acid bromide to give 1.

An attempt to intercept an ylide intermediate in this reaction by carrying out the synthesis in the presence of trifluoroacetophenone failed, since sodium dibutyl phosphite was found to react readily with the ketone. The ¹⁹F nmr and ³¹P nmr spectral data suggest that the product of this reaction is the enol phosphate.

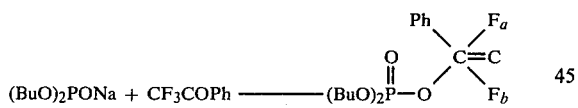

¹⁹F nmr: $F_a$:δ = 95.2(d,d) J(F,F) = 55 Hz, J(F,P) = 7.8 Hz
$F_b$:δ = 108.0(d,d) J(F,F) = 55 Hz, J(F,P) = 10.9 Hz
³¹P nmr: δ = 3.8 (d,d) J(P,$F_a$) = 5.6 Hz K(P,$F_b$) = 9.4 Hz A more direct synthesis of the bis(phosphonates) would be from the reaction of (RO)₂PONa with CF₂Br₂. Sodium dibutyl phosphite reacted rapdily with the evaluation of heat with CF₂Br₂ in hexane. When an excess of CF₂Br₂ was employed both (BuO)₂P(O)CF₂Br and (1) were formed in a 1.4/1 ratio. The use of a 2:1 stoichiometry of phosphite anion to CF₂Br₂ again resulted in the formation of (BuO)₂P(O)CF₂Br and (1) in approximately the same ratio. Any inert, non-protic solvent may be used, although good results are obtained using toluene.

A more direct synthesis of the bis(phosponates) would be from the reaction of (RO)₂PONa with CF₂Br₂. Sodium dibutyl phosphite reacted rapidly with the evolution of heat with CF₂Br₂ in toluene. When an excess of CF₂Br₂ was employed both (BuO)₂ P(O)CF₂Br and (1) were formed in a 1.4/1 ratio. The use of a 2:1 stoichiometry of phosphite anion to CF₂Br₂ again resulted in the formation of (BuO)₂P(O)CF₂Br and (1) in approximately the same ratio.

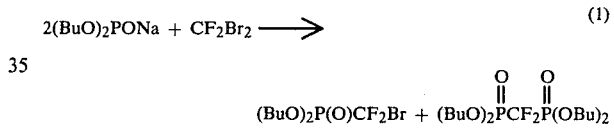

Apparently, a side reaction occurs which consumes (BuO)₂PONa in a non-productive step. The reaction between (BuO)₂PONa and $$\underset{\text{O}}{(BuO)_2 \overset{\|}{P}-Br}$$

(formed in the initial stage of the reaction) would be a likely candidate.

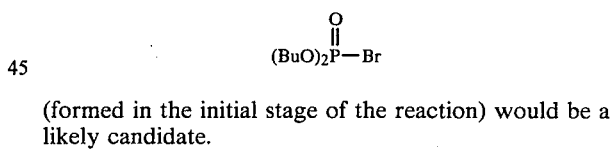

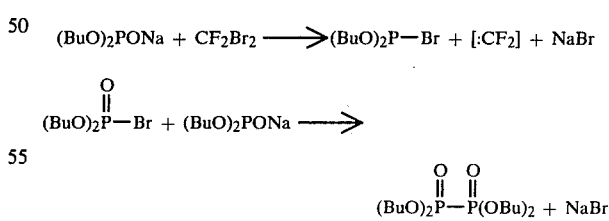

Generally, an inert hydrocarbon solvent such as hexane, a non-protic solvent, is used for the reaction. The reaction is exothermic and therefore no heating is required. For safety sake, it is desirable to cool the reactants and mix them slowly with agitation.

DETAILED DESCRIPTION OF THE INVENTION

The following examples serve to illustrate the invention.

EXAMPLE 1

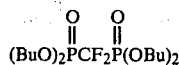
(BuO)$_2$PCF$_2$P(OBu)$_2$ (with P=O on both)

To a solution of

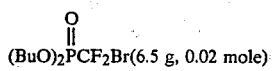
(BuO)$_2$PCF$_2$Br (6.5 g, 0.02 mole)

in dry hexane (40 ml) cooled in an ice water bath was added slowly via syringe a solution of (BuO)$_2$PONa in hexane (25 ml, 0.02 mole). The (BuO)$_2$PONa solution was prepared by the reaction of Na metal (2 g, 0.087 mole) and (BuO)$_2$POH (16.8 g, 0.087 mole) in 80 ml dry hexane. This afforded a solution of concentration approximately 0.8 M. After stirring for four hours, the mixture was poured into water (50 ml) and dried over anydrous Na$_2$SO$_4$. The hexane was removed at room temperature via rotary evaporation at reduced pressure and the residue distilled to give 4.1 g (47%) of

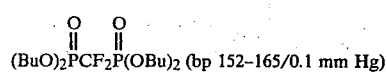
(BuO)$_2$PCF$_2$P(OBu)$_2$ (bp 152–165/0.1 mm Hg)

as well as 1.3 g (27%) (BuO)$_2$PCF$_2$H(bp 170°/3.6 mm Hg).

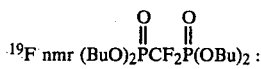
$^{19}$F nmr (BuO)$_2$PCF$_2$P(OBu)$_2$:

δ=121.6 (t) J=87 Hz; $^1$H nmr: δ=0.8–1.1 (m,3H), δ=1.1–1.9 (m,4H), δ=4.0–4.4 (m, 2H); $^{31}$P nmr: δ=−3.7 (t) J=86 Hz; $^{13}$C nmr: δ=13.5 (s) (CH$_3$—), δ=18.6 (s) (CH$_3$CH$_2$), δ=32.5 (3 peaks separated by 2.9 Hz-CH$_2$CH$_2$O), δ=68.9 (3 peaks separated by 3.7 and 2.9 Hz—CH$_2$O), δ=116.3 (t,t) J(C,P)=187 Hz J(C,F)=279 Hz (—CF$_2$—).

Analysis: Calculated for C$_{17}$H$_{36}$F$_2$O$_6$P$_2$: %C=46.79 %H=8.26

Found: % C=46.79. %H=8.27.

EXAMPLE 2

(EtO)$_2$PCF$_2$P(OEt)$_2$

Diethyl phosphite (9.0 g, 0.065 mole) was syringed into a mixture of sodium metal (1.5 g, 0.065 mole) in dry hexane (50 ml). After the initial vigorous reaction had subsided, the solution was heated to reflux until the sodium metal had completely dissolved. The mixture was cooled in an ice bath and

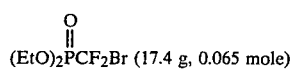
(EtO)$_2$PCF$_2$Br (17.4 g, 0.065 mole)

added slowly via syringe. The reaction was rapid and the white solid dissolved and was replaced by a gray-green precipitate. After stirring for one hour at room temperature, water (50 ml) was added and three layers formed. The middle aqueous layer was separated and discarded; the top and bottom layers were combined and dried over anhydrous sodium sulfate. The hexane was removed by rotary evaporation at aspirator pressure and the residue distilled to yield 2.7 g (13%)

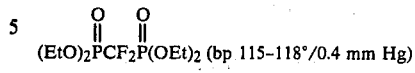
(EtO)$_2$PCF$_2$P(OEt)$_2$ (bp 115–118°/0.4 mm Hg)

as well as a forerun (3 g) consisting of a 1:1 mixture of (EtO)$_2$

PCF$_2$Br and (EtO)$_2$PCF$_2$H(bp 46.5–47.5°/0.4 mm Hg).

The $^{19}$F nmr spectrum of

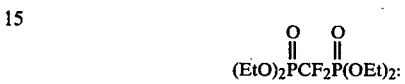
(EtO)$_2$PCF$_2$P(OEt)$_2$:

δ=122.0 (t) J=87 Hz; $^1$H nmr: δ=1.40 (t) J=7 Hz (CH$_3$);δ=4.39 (d,q) J (H,H)=7 Hz, J(H,P) δ=3.8 Hz (CH$_2$O); $^{31}$P nmr: δ=−3.5 (t) J=86 Hz; $^{13}$C nmr: δ=16.4 (s) (CH$_3$—);δ=65.3 (d) J=2.9 Hz; δ=116.2 (t,t) J(C,P)=187 Hz, J(C,F)=279 Hz.

Analysis: Calculated for C$_9$H$_{20}$F$_2$O$_6$P$_2$: %C=33.33%H=6.17.

Found: %C=33.41 %H=6.32.

EXAMPLE 3

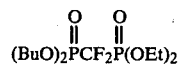
(BuO)$_2$PCF$_2$P(OEt)$_2$

Dibutyl phosphite (6.26 g, 0.032 mole) was added to sodium metal (0.74 g, 0.032 mole) in dry hexane (30 ml) and the mixture stirred overnight under an inert atmosphere. After dissolution of the sodium, the solution was transferred to a 60 ml constant addition funnel and added slowly dropwise to an ice cold solution of

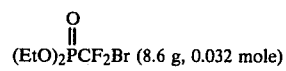
(EtO)$_2$PCF$_2$Br (8.6 g, 0.032 mole)

in hexane. A check of the $^{19}$F nmr spectrum of the solution after completion of the addition revealed that all of

(EtO)$_2$PCF$_2$Br had been consumed and that three triplets were present at

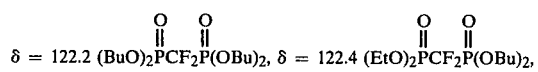
δ = 122.2 (BuO)$_2$PCF$_2$P(OBu)$_2$, δ = 122.4 (EtO)$_2$PCF$_2$P(OBu)$_2$,

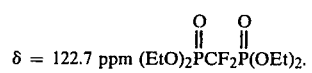
δ = 122.7 ppm (EtO)$_2$PCF$_2$P(OEt)$_2$.

Water (50 ml) was added to the reaction mixture and the organic layer was separated and washed again with water. The two aqueous layers were combined and examined by $^{19}$F nmr. The $^{19}$F nmr spectrum revealed that the aqueous layers contained

as the only fluorine containing compound. The organic layer was dried over anhydrous MgSO₄, the hexane removed via rotary evaporation at aspirator pressure and the residue distilled to yield two fractions. The first contained

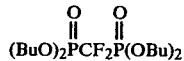

and the unsymmetrical bis (phosphonate)

in about a 3:1 ratio (bp 126°–136°/0.2 mm Hg). The second fraction contained the same products in a 1:2 ratio (bp 147–153/0.2 mm Hg); no

was observed. ¹H nmr: butyl protons of

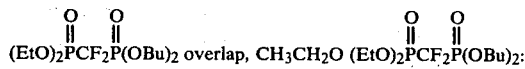

$\delta = 1.38$ (t) $J = 7$ Hz; ¹⁹F nmr (EtO)₂PCF₂P(OBu)₂:

$\delta = 121.7$ (t) $J = 87$ Hz; ³¹P nmr: $\delta = -3.7$ (t) $J = 86$ Hz (overlap of

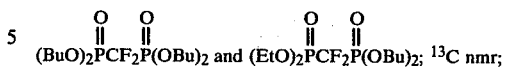

; ¹³C nmr;

(butyl carbons of (BuO)₂PCF₂P(OBu)₂ and

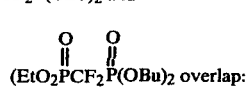

overlap:

$\delta = 13.5$ (s), $\delta = 186$ (s), $\delta = 32.5$ (t) $J = 3$ Hz, $\delta = 68.9$ (t) $J$ 3 Hz (butyl carbons); $\delta = 16.4$ (t) $J = 3$ Hz (CH₃CH₂O), $\delta = 65.4$ (d) $J = 3$ Hz (CH₃CH₂O); $\delta = 116.2$ (t,t) $J$ (C,P) = 188 Hz, $J$ (C,F) = 279 Hz. The assignments of the butyl carbons and the ethyl carbons was made by comparison to the spectral data of

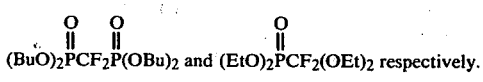 respectively.

Using the same reaction procedure as set forth in the examples it is possible to make compounds of the formula

wherein R is 1 to 12 carbons, preferably 1 to 6.

These compounds can be used in the following ways: as detergents and as chelating agents for ions.

We claim:

1. The compound:

* * * * *